United States Patent [19]

Kostic et al.

[11] Patent Number: 4,997,758

[45] Date of Patent: Mar. 5, 1991

[54] CROSS-LINKING PROTEINS WITH BIMETALLIC TETRACARBOXYLATE COMPOUNDS OF TRANSITION METALS

[75] Inventors: Nenad M. Kostic; Jian Chen, both of Ames, Iowa

[73] Assignee: Iowa State University Research Foundation, Inc., Ames, Iowa

[21] Appl. No.: 297,583

[22] Filed: Jan. 17, 1989

[51] Int. Cl.$^5$ .................. C12N 11/02; C12N 11/06; C07K 17/02; C07K 17/06
[52] U.S. Cl. ................................ 435/177; 435/176; 435/181; 530/356; 530/811; 530/812; 530/816
[58] Field of Search ............... 435/174, 176, 177, 180, 435/181; 530/356, 420, 421, 810, 811, 812, 816

[56] References Cited

PUBLICATIONS

Zaborsky, O. R., Biomedical Applications of Immobilized Enzymes and Proteins, vol. 1, 1977, pp. 25–35.
Nakatsuji et al., Chemical Abstracts, 98: 20661of, 1983, p. 525

*Primary Examiner*—David M. Naff
*Attorney, Agent, or Firm*—Zarley, McKee, Thomte, Voorhees & Sease

[57] ABSTRACT

Stable cross-linked complexes of transition-metal tetracarboxylates and proteins are formed. The preferred transition-metal is rhodium. The protein may be collagen or an enzyme such as a proteolytic enzyme.

16 Claims, No Drawings

CROSS-LINKING PROTEINS WITH BIMETALLIC TETRACARBOXYLATE COMPOUNDS OF TRANSITION METALS

GRANT REFERENCE

This invention was made with Government support under Contract No. W-7504-ENG-82 awarded by the Department of Energy. The Government has certain rights in this invention.

BACKGROUND OF THE INVENTION

Proteins are biologically synthesized macromolecules having various roles in living systems. Enzymes are a particular variety of biologically active proteins which catalyze specific reactions. Presently, enzyme technology is used in many industrial applications and in basic research, such as, for example, medical research, food processing and preservation, the production of fermented beverages, the production of pharmaceuticals, and the analytical determination of the concentration of various metabolites in foods.

Enzymes are highly specific in their biological activity and generally catalyze a particular reaction at a very high rate compared to the corresponding reaction occurring at room temperature without biological catalysis. One enzyme may show catalytic activity with respect to a number of substrates upon which it can act. Accordingly, a given enzyme may catalyze the synthesis or degradation of more than one substrate.

Many enzymes are found in nature in very small quantities. Accordingly, their isolation, purification and use are limited to small-scale operations in view of the expense and time needed to isolate them in a usable amount.

Enzymes have been used extensively in industrial processes both in soluble and insoluble forms. The use of soluble enzymes for industrial processes, however, is limited by their cost, their instability, and the difficulties in recovering them after the operation.

These disadvantages have been circumvented by a new technology based on enzyme immobilization, i.e. enzyme attachment to solid support materials. A number of techniques have been developed for enzyme immobilization, of which the major ones are intramolecular cross-linking and covalent linking to supports. Support materials in different forms—beads, membranes and fibers—can be used. The most common support material for enzyme reactors are beads or porous particles which can be packed into columns or used in stirred-tank reactors. Another form is the sheet or membrane form which can be used in pressure cells.

The advantage of utilizing such immobilized or insoluble enzymes resides in the possibility of acting catalytically with an enzyme on a substrate stream in a continuous way with no need of separating the enzyme from the product obtained by the catalytic reaction.

In short, many studies in biochemistry, biophysics, and chemical biology involve covalent cross-linking of enzymes and other proteins to different biomolecules and to carrier materials. All of the reagents developed to date for this purpose are bifunctional organic compounds. Some of them are selective, usually towards amino and sulfhydryl groups in the amino acid side chains; some, such as photogenerated nitrenes, are non-selective. Besides selectivity, desirable properties of cross-linking reagents are solubility in water; reactivity under mild, preferably physiological, conditions; stability; and cleavability, so that the linked species can be separated in their native forms.

All of these required properties can be achieved with inorganic reagents. Various spectroscopic and chemical properties render transition-metal complexes uniquely suited for specific covalent binding to amino-acid side chains in proteins and to other biological macromolecules.

An ideal cross-linking agent should be one which enhances the stability of the polymer under a wide variety of conditions. Also, an ideal cross-linking agent for proteins should be one which does not interfere with the activity of the protein, and in particular does not inactivate or denature the protein. Moreover, as earlier mentioned, ideal cross-linking agents should be soluble in water; they should also be active in neutral solutions, preferably in the physiological range of pH values.

Accordingly, a primary objective of the present invention is to provide stable cross-linked complexes between transition metal carboxylates and proteins.

A further objective of the invention is to provide a method of forming stable cross-link complexes between binuclear transition-metal compounds and proteins.

An even further objective of the present invention is to provide useful and improved cross-linked enzymes, with the cross-linking being between enzymatic proteins and dirhodium tetracarboxylates.

The method of accomplishing each of the above objectives of the present invention, as well as others, will become apparent from the detailed description of the invention which follows hereinafter.

SUMMARY OF THE INVENTION

Stable, cross-linked complexes of binuclear transition-metal compounds and proteins are formed by treating in an aqueous medium a bimetallic transition-metal compound of the formula: $M_2(RCOO)_4$, wherein M is a transition metal and R is a $C_1$ to $C_{18}$ alkyl, with a protein (L) to form a cross-linked complex of the formula $M_2(RCOO)_4L_2$.

DETAILED DESCRIPTION OF THE INVENTION

This invention relates to bimetallic tetracarboxylato compounds of transition metals as reagents for cross-linking of proteins. The reagents have the formula: $M_2(RCOO)_4$, wherein M is a transition metal and, R is $C_1$ to $C_{18}$ alkyl. Binding of protein molecules (designated L) results in the complexes of the formula $M_2(RCOO)_4L_2$.

M can be any transition metal, but is preferably rhodium, palladium, platinum, ruthenium, osmium, copper and the like. Most preferably M is rhodium.

R represents an alkyl group within the range of $C_1$ to $C_{18}$, preferably $C_1$ to $C_4$, and most preferably methyl.

L represents two similar or dissimilar protein molecules and various biologically active protein materials, including the most preferred enzymes. The enzyme may be hydrolases, isomerases, ligases, lyases, oxido-reductases, or transferases. The biological material may also be collagen and other biologically active protein polymeric materials of the types earlier mentioned.

The reaction between the bimetallic transition-metal tetracarboxylate and the protein occurs in neutral aqueous medium. The new cross-linking reagents are compatible with weakly acidic and weakly basic, as well as neutral media. Since they are stable throughout the usual pH range of protein stability, incubation can be carried out under physiological conditions. The preferred pH range is from about 7 to about 10.

This invention introduces bimetallic complexes as reagents for cross-linking of proteins. The presence of metal-metal bonds or of bridging ligands, or of both, enriches the chemistry of such complexes and makes them potentially versatile as protein links. Dirhodium-(II)-u-tetracarboxylates, $Rh_2(RCOO)_4$, are especially suitable for binding to biological macromolecules for the following reasons. Since each metal atom has an unobstructed vacant coordination site, various ligands readily form adducts of the types $Rh_2(RCOO)_4L$ and $Rh_2(RCOO)_4L_2$. The short and strong

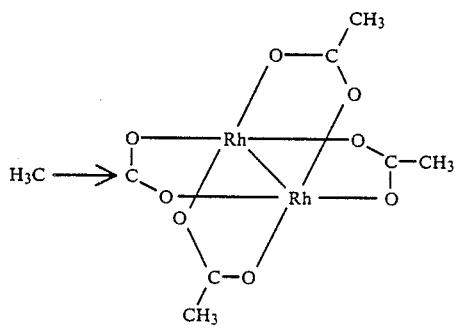

Rh(II)-Rh(II) bond and the entire $Rh_2(RCOO)_4$ lantern remain intact in the reactions with almost all of the ligands L. Variability of the bridging carboxylate, i.e., of the group R, permits purposeful changes in the hydrophilicity or lipophilicity of the complex and allows adjustment in the Lewis acidity of the metal atoms. The acetate complex is designated $Rh_2(OAc)_4$. It is preferred because it is the most widely studied member of the series and because the strong $^1H$ NMR signal of the four equivalent methyl groups permits a direct detection of the complex even in the presence of the protein with its multitude of aliphatic C—H bonds.

The following examples are offered to further illustrate but not limit the process and cross-linked complexes of the present invention.

EXAMPLES

For these examples, the proteins, amino acids, amino-acid derivatives, 4,4'-bipyridyl, and Sephadex G 75-50 were obtained from Sigma Chemical Co.; deuteriated solvents and $Rh_2(OAc)_4$, from Aldrich Chemical Co. Distilled water was demineralized further in a Barnstead Nanopure II apparatus.

Purification of Cytochrome c. Ferricytochrome c from horse heart (preparations of types III and VI from Sigma) were fully oxidized with $K_3[Fe(CN)_6]$; dialyzed in an Amicon ultrafiltration cell with a YM-5 membrane under the pressure of nitrogen; and chromatographed, with 85 mM phosphate buffer at pH 7.0 as an eluent, on a column of CM 52 cation exchanger, obtained from Whatman. Only the major fraction, containing ca. 85% of the commercial protein, was used in subsequent experiments.

Molecular masses were determined by size-exclusion chromatography on a column of Sephadex G 75–50, sized 1.5×70 cm, at 4° C. The eluent was 85 mM phosphate buffer at pH 7.0. The flow rate of 10.0 mL $h^{-1}$ was maintained with a peristaltic pump. Absorbance was measured with an ISCO V-4 detector equipped with a strip-chart recorder. The following proteins, whose molecular masses in kDa are given in parentheses, were used for calibration of the column before every determination: aprotinin (6.5), horse-heart cytochrome c (12.5), carbonic anhydrase (29.0), and bovine albumin (65.0). For greater accuracy, elution times at constant flow rate, rather than elution volumes, were measured.

The UV-vis spectra were recorded with an IBM 9430 spectrophotometer, whose monochromator contains two gratings. The spectra of the model complexes $Rh_2(OAc)_4L_2$ in aqueous solution were measured in the presence of excess ligand L, to ensure complete formation of the diadducts. The IR spectra were recorded with an IBM IR98 Fourier-transform instrument, whose sample chamber was flushed with purified nitrogen. Dried $Rh_2(OAc)_4L_2$ model complexes, lyophilized cytochrome c, and lyophilized $Rh_2(OAc)_4(cyt)_2$ complex were taken into Nujol mulls, which were then smeared on the CsI plates.

The $^1H$ NMR spectra at 300MNz were recorded with a Nicolet NT300 spectrometer. The "inorganic" samples (complexes with nonprotein ligands L) were dissolved in $D_2O$ or in DMF-$d_7$, and the residual protons in these solvents were used as standards for chemical shifts. The protein-containing samples were dialyzed repeatedly into $D_2O$ by ultrafiltration and then lyophilized with successive portions of $D_2O$ in order to replace the exchangeable H atoms with deuterium.

The X-band EPR spectra were recorded at 5K with a Bruker ER200-SRC instrument, equipped with an Oxford Instruments ESR900 cryostat. A double rectangular cavity had a nominal frequency of 9.56GHz; modulation frequency was 100 kHz. The protein-containing samples were fully oxidized with $[Co(phen)_3](ClO_4)_3$ and the oxidant removed by dialysis into 85 mM phosphate buffer at pH 7.0.

Differential-pulse and cyclic voltammograms were obtained with an IBM EC225 electrochemical analyzer equipped with a Houston Instrument Omnigraph 200 XY recorder. A BAS cell assembly consisted of an Ag/AgCl couple as reference, a Pt wire as auxiliary, and a 1.6-mm Au disk as working electrode. The composition of the solution was as follows: ca. 0.5 mM in cytochrome c, 10 mM in 4,4'-bipyridyl as a mediator, and 100 mM in $NaClO_4$, all dissolved in 85 mM phosphate buffer at pH 7.0. A small, jacketed 5-mL cell permitted experiments with 2-mL samples. The solutions were deoxygenated by gentle bubbling of argon and a blanket of this gas was maintained during the measurements.

Ferricytochrome c was incubated with $Rh_2(OAc)_4$ in 85 mM phosphate buffer at pH 7.0. The protein concentration was 2.0 mM, usually 25 mg (2.0 umol) in 1.0 mL of the buffer. The concentration of the linking reagent was varied systematically from 1.0 to 5.0 mM, i.e., from 0.44 to 2.2 mg (1.0 to 5.0 umol) in 1.0 mL of the buffer; incubation time was also varied. The optimal yield, 20% per incubation on the average, was achieved with 2.0 mM protein and 5.0 mM $Rh_2(OAc)_4$ in 2 days. Because the unreacted protein is easily recovered intact by chromatography (see below) and because it can be incubated anew, the overall yield of up to 100% can be achieved by repeated incubations.

Size-exclusion chromatography of the reaction mixture yielded three well-separated major bands. The first two of them, designated I and II, contained cytochrome c and were red-brown. Their apparent molecular masses (averages of several measurements) were $34 \pm 1$ and $12.5 \pm 0.5$ kDa, respectively. These values correspond, respectively, to two and one molecule of cytochrome c. (The small discrepancy between the determined and expected molecular masses is fully explicable in terms of the mechanism of the size-exclusion chromatography; there are many reliable precedents for such discrepancies.) The third band, designated III, contained the unspent $Rh_2(OAc)_4$ and was bluish green. When the incubation was carried out at pH 5.0 (in 85 mM acetate buffer), no cross-linking took place. Only a red-brown band of the unspent cytochrome c, having the molecular mass of 12.5 kDa, and a blue band of the unspent $Rh_2(OAc)_4$ were obtained.

The cross-linking experiments (incubation at pH 7.0 and size-exclusion chromatography) were performed in the standard way with native tuna-heart cytochrome c and with horse-heart cytochrome c tagged at His 33 with a $Pt(trpy)^{2+}$ group. In the latter case the yield of the diprotein complex was much lower (ca. 5%) than with the native horse-heart cytochrome c. In the former case the diprotein complex was not obtained at all.

Stability of the diprotein complex was determined as follows. $Rh_2(OAc)_4(cyt)_2$ was incubated at room temperature, in 85 mM buffers at different pH values, without or with added nucleophiles; and the composition of the solutions was determined after 2–3 days by size-exclusion chromatography. All the solutions were 50 $\mu M$ in the diprotein complex and 100 $\mu M$, 1 mM, or 100 mM in the nucleophile. The cleavage yield is the ratio between the amounts of the monomeric and of the total (monomeric plus dimeric) cytochrome c. Incubation at pH 7.0 (in phosphate buffer) produced less than 5% of the monomeric cytochrome c; similar incubation at pH 5.0 (in acetate buffer) produced 16% of it; the presence of a 2-fold excess of $NaN_3$ at pH 7.0 caused the cleavage yield of 8%, both 2-fold and 20-fold excesses of NaCN at pH 7.0 raised this yield to 30–35%; 2000-fold excess of 2-mercaptoethanol at pH 7.0 caused nearly complete (greater than 80%) displacement of the protein molecules from the $Rh_2(OAc)_4(cyt)_2$ complex.

The diprotein complex $Rh_2(OAc)_4(cyt)_2$ is more stable thermodynamically than would be expected on the basis of the equilibrium studies of $Rh_2(OAc)_4L_2$ model complexes with histidine and histidine-containing dipeptides as ligands L. Prolonged standing at pH 7.0, at room temperature does not cause appreciable dissociation of the diprotein complex. Even the good nucleophiles such as $CN^-$ and $N_3^-$ anions, present in excess, only partially displace the protein ligands. A large excess of the highly nucleophilic 2-mercaptoethanol, however, can extrude the linking reagent and restore the native cytochrome c.

While applicants do not wish to be bound by theory of operation of the invention, the enhanced stability of the protein complex may result from two causes. First, the bulky and rather hydrophobic protein molecules may shield the bimetallic link from attack by the solvent (water) and by the potential ligands present in solution. Second, the oxygen atoms constituting the $RhO_4$ faces may form hydrogen bonds with side chains of some amino-acid residues. Simulation by molecular graphics of the $Rh_2(OAc)_4$ binding to the imidazole ring of His 33 corroborates this second hypothesis.

Spectroscopic (UV-vis, H NMR, and ESR) and electrochemical (differential-pulse and cyclic voltametric) measurements show that the structural and redox properties of cytochrome c are not perturbed by cross-linking.

In short, it can be seen that the transition metal tetracarboxylate complexes with proteins, described in the present invention, are useful means of cross-linking proteins to provide increased stability, enhanced usefulness, and provide cross-link protein in a manner which is non-injurious, dilatorious or harmful to any available uses of the biologically active protein materials.

What is claimed is:

1. A method of forming cross-linked complexes between binuclear transition-metal compounds and proteins, said method comprising:
   (a) a reacting rhodium tetracarboxylate compound having the formula: $Rh_2(RCOO)_4$ wherein R is a $C_1$ to $C_{18}$ alkyl, with a protein (L) to form a cross-linked complex of the formula: $Rh_2(RCOO)_4L_2$.

2. The method of claim 1 wherein R is $C_1$ to $C_4$ alkyl.

3. The method of claim 1 wherein L is a histidine-containing protein.

4. The method of claim 1 wherein L is an enzyme.

5. The method of claim 1 wherein L is collagen.

6. The method of claim 1 wherein said reacting occurs in an aqueous medium.

7. The method of claim 6 wherein said reacting occurs at a pH of at least 7.0.

8. The method of claim 7 wherein said pH is from about 7.0 to about 10.0.

9. A stable cross-linked complex of a rhodium tetracarboxylate compound and a protein having the formula: $Rh_2(RCOO)_4L_2$, wherein R is $C_1$ to $C_{18}$ alkyl, and L is a protein.

10. The complex of claim 9 wherein R is $C_1$ to $C_4$ alkyl.

11. The complex of claim 6 wherein R is methyl.

12. The complex of claim 9 wherein the protein is of animal origin.

13. The complex of claim 9 wherein the protein is of plant origin.

14. Stable cross-linked dirhodium tetracarboxylate complexes having the formula: $Rh_2(RCOO)_4L_2$, wherein R is $C_1$ to $C_4$ alkyl, and L is an enzyme.

15. The complexes of claim 14 wherein said enzyme is selected from the group consisting of hydrolases, isomerases, liagases, lyases, oxido-reductases, or transferases.

16. The complexes of claim 15 wherein said enzyme is a proteolytic enzyme.

* * * * *